United States Patent [19]

Weiner et al.

[11] Patent Number: 4,740,466
[45] Date of Patent: Apr. 26, 1988

[54] INDUCTION OF SETTLEMENT AND METAMORPHOSIS IN *CRASSOSTREA VIRGINICA* BY MELANIN-SYNTHESIZING BACTERIA

[75] Inventors: Ronald M. Weiner, Rockville; Rita R. Colwell, Bethesda; Dale B. Bonar, Gambrillis, all of Md.; Steven L. Coon, Falls Church, Va.

[73] Assignee: Research Corporation, New York, N.Y.

[21] Appl. No.: 567,023

[22] Filed: Dec. 30, 1983

[51] Int. Cl.$^4$ .................. C12N 1/20; C12P 19/04; C12P 13/22; C12R 1/01
[52] U.S. Cl. ................... 435/253; 435/101; 435/108; 435/822
[58] Field of Search ............ 435/253, 909, 101, 822, 435/874, 108

[56] References Cited

PUBLICATIONS

Yoshida et al., "Production of 3,4-dihydroxyphenyl-l-alanine (L-dopa) and its Derivatives by Vibrio Tyrosinaticus", Agr. Biol. Chem., 37(9), 2121–2126, 1973.

Pomerantz et al., "Purification and Properties of Tyrosinases from Vibrio Tyrosinaticus", Archives of Biochemistry and Biophysics, 160; 73–82, 1974.

Ivins et al., "Isolation and Characterization of Melanin-Producing (mel), Mutants of Vibrio Cholerae", Infection and Immunity, vol. 27, pp. 721–729, 1980.

Ivins et al., "Factors Affecting Phaeomelanin Production by a Melanin-Producing (mel) of Mutant of Vibrio Cholerae Infection and Immunity, vol. 34, pp. 895–899, 1981.

*Primary Examiner*—Elizabeth Weimar
*Attorney, Agent, or Firm*—Scully, Scott, Murphy & Presser

[57] ABSTRACT

The present invention relates to the discovery of a new bacterium, *alteromonas colwellii*, which has been found to attract oyster larvae by the production of a compound involved in melanin synthesis. More specifically, the present invention contemplates a method for inducing the settlement and metamorphosis of *Crassostrea virginica* larvae by induction with certain metabolic substances produced by the present bacterium and its mutagenically altered variants. Furthermore, the present invention is directed to other and derivative metabolic products which can be employed for their desired utility and application.

2 Claims, 7 Drawing Sheets

NORMAL ROD STRUCTURE

FIG. 1

FORMING OF SLANTED INDENTATIONS
ACROSS THE CELL SURFACE

FIG. 2

ADVANCED STAGE IN SPIRAL FORMATION

FIG. 3

AN ELONGATED CELL WITH SPIRAL FORMS IN THE BACKGROUND

FIG. 4

GENERAL VIEW OF ABERRANT VS.
NORMAL CELL MORPHOLOGIES

INDUCTION OF SETTLEMENT AND METAMORPHOSIS IN *CRASSOSTREA VIRGINICA* BY MELANIN-SYNTHESIZING BACTERIA

BACKGROUND OF THE INVENTION

The present invention relates to the discovery of a new bacterium which has been found to attract oyster larvae by the production of a compound involved in melanin synthesis. More specifically, the present invention contemplates a method for inducing the settlement and metamorphosis of *Crassostrea virginica* larvae by induction with certain metabolic substances produced by the present bacterium and its mutagenically altered variants. Furthermore, the present invention is directed to other and derivative metabolic products which can be employed for their desired utility and application.

The formation of pioneer microbial communities on submerged surfaces appears to be beneficial to subsequent attachment and development of many invertebrate larvae. A number of investigations have established a general pattern of periphytic succession for colonization of clean surfaces immersed in seawater. In the initial phase after possible coating by organic matter, bacteria attach to such a surface and begin to grow, forming microcolonies within several hours. Subsequently, diatoms, fungi, protozoans, micro-algae and other microorganisms attach to the surface, forming what has been termed the primary slime layer. This primary microbial colonization appears to be a prerequisite for the final stage of succession in which microorganisms, viz., invertebrates, attach and grow on the surface. Although most surfaces are eventually colonized, the rapidity and extent of the process depends on the nature of the surface material, the prevailing environmental conditions and the composition of the periphytic populations.

Two invertebrate species for which some information has been ascertained concerning the effect of the periphytic organisms on their induced metamorphosis are the sea urchin, *Lytechinus pictus*, and the hydroid, *Hydractinina echinata*. It has been determined that for Lytechinus, the responsible factor is a low molecular weight bacterial by-product, probably proteinaceous having a molecular weight less than 5000 daltons. It has also been found that planulae larvae of Hydractinia metamorphose in response to a product emitted by certain marine, gram-negative bacteria at the end of their exponential growth phase. If these bacterial cultures are subjected to osmotic shock, the activity shows up in the supernatant, suggesting that the critical product is a soluble factor rather than a bound one. When Hydractinia are kept in sterile conditions, they do not metamorphose.

In a series of experiments designed to determine the physiological mechanism by which the stimulus activates metamorphosis, it has been demonstrated that the inducer may operate by stimulating the $Na^+/K^-$ATPase of larval cell membranes. Such findings are the first real steps toward understanding how larvae can mount a broad spectrum morphogenetic response to specific environmental stimulation. Moreover, recent reports have shown that Vibrio sp. excretes a product that induces metamorphosis of the cnidarian, *Cassiopea andromeda*. Other investigations demonstrate that larvae of the marine annelid, *Janua brasiliensis*, settle on certain microbial films and that certain specific bacteria may induce metamorphosis. These observations suggest that the processes are mediated by larval lectins binding to extracellular polysaccharides or glycoproteins, produced by the bacteria.

In both the natural environment and in oyster mariculture operations, the setting process, whereby planktonic oyster larvae alight on an oyster shell or plastic sheet and undergo metamorphosis to form attached oyster spat, is crucial to successful oyster development. It is also known that the larvae of *Ostrea edulis*, the European oyster, prefer setting on surfaces covered with a film of bacteria and diatoms. Natural periphytic microbial populations are, therefore, significant in successful oyster setting. The same situation is likely to be true of oyster mariculture, since a rich source of bacterial flora has been associated with oyster larvae and larval food sources in hatcheries. In some cases, bacteria have also been implicated in the death of oyster larvae. Since the presence of microorganisms significantly affects oyster development, improved knowledge of the biology of these microorganisms and particularly an understanding of their beneficial and/or deleterious effects on developing oysters, will further improve oyster setting and development in both natural and artificial settings.

Oyster larvae display three characteristic patterns toward organic compounds and microorganisms, i.e., positive, inactive and negative chemotaxis. In one particular study, a marine pseudomonad was attractive to larvae while a marine yeast elicited no response. It has also been suggested that an alga, Isochrysis, may produce extracellular oyster attractant. Conversely, it is known that oyster larvae do not set preferentially on surfaces to which a marine isolate, *Hyphomonas neptunium*, is affixed. It is believed that *H. neptunium* does not antagonize settlement, but rather that it competitively establishes itself on surfaces and excludes bacterial species which would be beneficial to oyster settlement.

The question, however, of which of the periphytic microorganisms and which of their products specifically attract or promote the setting and subsequent development of oyster larvae has not been answered heretofore. Free swimming larvae, shortly after spawning, seek a suitable place to settle and attach themselves. A number of environmental conditions are involved in settlement, salinity and nutritional availability are probably the most important. But once larvae are satisfied with these initial conditions, they appear to respond to a biochemical cue to settle and attach themselves. That biochemical cue is released by a pigmented bacterium which adheres strongly to surfaces such as oyster shells and which is the subject of this invention.

SUMMARY OF THE INVENTION

It is, therefore, one object of the present invention to provide a marine bacterium which is capable of inducing the settlement and metamorphosis of *Crassostrea virginica* larvae.

Another object of this invention is to provide a method for inducing the settlement and metamorphosis of *Crassostrea virginica* larvae.

A further object of the present invention is to isolate and purify the metabolic products of the present bacterium and those of its mutagenically altered variants.

Still another object of this invention is to employ the isolated metabolic products of the present bacteria for their desired utility.

These and other objects are achieved by the discovery of a melanin-synthesizing marine bacterium, designated LST, which has been mutagenically altered in accordance with this invention to provide two particular variants thereof, designated DIF and HYP. These bacteria have been taxonomically identified as a new species of the genus Alteromonas, a genus established to include a diverse array of polarly flagellated, aerobic marine bacteria. These bacteria have been named and characterized as *Alteromonas colwellii*. Each bacterium has been deposited with the American Type Culture Collection (ATCC) and have been accorded the accession numbers 39565, 33887 and 33888, respectively. LST and its variants, DIF and HYP, and/or any of their variants, can be employed in a process for inducing the settlement and metamorphosis of *Crassostrea virginica* larvae. This process may be employed in a natural or artificial environment, e.g., a mariculture operation, to induce the setting process of oyster larvae during which process the larvae alight on cultch or other suitable surface materials, and undergo metamorphosis to form attached oyster spat. The present method can be effected by exposing the *Crassostrea virginica* larvae to the LST, DIF, HYP and/or any of their variant bacteria or the melanin and melanin precursor metabolic products thereof in an aqueous environment.

Moreover, certain metabolic products of the present bacteria can be isolated and employed for their desired utility. The DIF and HYP variants exhibit particularly heightened levels of production of these metabolic substances.

DETAILED DESCRIPTION OF THE INVENTION

In accordance with the present invention, a new melanin-synthesizing marine bacterium, designated LST, has been isolated in continuous and close association with oysters and can be employed in a process for inducing the settlement and metamorphosis of *Crassostrea virginica* larvae. Moreover, several metabolic products have been recovered from the present bacterium which are highly desirable for their industrial, experimental or medical utility.

Thus, among the many advantages of the present invention, it has been surprisingly discovered that the novel marine bacterium of this invention and, particularly, the mutagenically altered variants thereof, designated DIF and HYP, which have also been accorded the ATCC accession numbers 39565, 33887 and 33888, respectively, are capable of specifically inducing the setting and metamorphosis of *Crassostrea virginica* larvae by the production of certain metabolic products associated with melanin synthesis. These metabolic products, melanin, pheomelanin and dihydroxyphenylalanine have been found to have significant commercial, experimental and medical utility.

In more detail, LST and its related variants are Vibrio-like, aerobic, highly motile, gram-negative rods, with a guanosine to cytosine ratio of 45.6% and have been found to attract oyster larvae by production of a compound involved in melanin synthesis. The compound is most abundantly synthesized during the late stationary-decline phase of bacterial growth when the adenylate energy charge is 0.72 and the organism is undergoing morphological transition to the elongated helical form. The bacteria grow optimally in 35 ppt salt, and within a range of 15–75 ppt at 25° C. and do not produce spores. The bacteria readily attach to a variety of surfaces including, preferentially, glass and oyster shells, and also to plastic, aluminum, and the like. The biochemical characteristics of LST are set forth in Table 1 below. These bacteria have been taxonomically identified as a new species, *colwellii*, of the genus Alteromonas.

LST, DIF and HYP, though heterotrophic, have relatively simple nutritional requirements as set forth below in Table 2. Although serine and methionine alone do not support the growth of LST or its related variants, aspartic and glutamic acids, in combination with serine, methionine or each other, do sustain the organism. Therefore, either aspartic or glutamic acid could serve as a carbon and energy source. In practice, however, it is preferred that a growth medium of aspartic acid and a solution of inorganic salts be supplemented with glutamic acid to remedy the growth-limiting effects which may be observed after numerous subculturings.

LST and its mutagenically altered variants, particularly DIF and HYP, are marine bacteria that use amino acids but do not use carbohydrates, fail to ferment sucrose, mannose or arabinose (see Table 1), and fail to grow in a medium containing 1% glucose and salts solution.

In the stationary phase of growth, these bacteria routinely produce a reddish-brown pigment, which has been identified as a melanin and which bio-synthetic pathway has been discovered to mediate the interaction between the bacteria and the oyster larvae. Notably, oyster larvae must settle prior to metamorphosis and do so in response to a chemical cue, i.e., a positive chemotaxis. In this regard, it has been determined that the melanin macromolecule is actually a heteropolymer of a number of different monomeric precursors. Of particular importance is dihydroxyphenylalanine (DOPA), a melanin precursor which increases oyster spat attachment and thus supports the settling of larvae. DOPA is also known to have significant physiological applications, primarily acting as a neurotransmitter in humans and animals and is often used in the treatment of Parkinson's disease or other related nervous disorders.

Thus, in one aspect of the present invention, two mutagenically altered variants of the parent LST bacterium, designated DIF and HYP, have been isolated through conventional techniques such as, for example, mutagenesis with ethyl methane sulfonate (EMS) or ICR 191 (Institute of Cancer Research intercalating agent). Each of these variants exhibit unique characteristics relative to the production of the metabolic pigment products, e.g., melanin, pheomelanin, DOPA, tyrosine, tyrosinase and related enzymes. Each of the variants can therefore be selectively employed in a process for the settlement and metamorphosis of oyster larvae. By the term variant or mutant is meant the genetic derivative of the parent bacterium which is obtained by single or multiple base substitutions, deletions, insertions or inversions whether spontaneously or artificially induced.

Moreover, the LST, DIF and HYP strains each produce an additional exopolymer as a product of their metabolism. This acid polysaccharide has been found to have excellent utility as a marine cement, a water-proofing material and an emulsifying agent which can be employed, for example, in the clean-up and removal of oil and organic spills.

In one particular embodiment of this invention, each of the present bacteria or their variants can be employed in a process for inducing the settlement and metamorphosis of *Crassostrea virginica* larvae. Accordingly, the bacteria are cultured in a growth medium and provided with a suitable surface material to which they can affix due to the production of the acid polysaccharide exopolymer. Oyster larvae are simultaneously or thereafter exposed to the bacteria or, alternatively, to their melanin or melanin precursor metabolic products including melanin, pheomelanin, DOPA, or mixtures thereof for a time and under conditions to effect larvae setting. Once settlement occurs, metamorphosis, i.e., maturation of the oyster larvae, naturally progresses in response to the micro-colonies of bacteria which develop on the provided surface material.

By way of explanation, although not wishing to be bound, it is believed that when sufficient numbers of bacteria are achieved, during the decline phase of growth., the bacterial colonies produce a high concentration of pigment, i.e., melanin and the precursor DOPA, which attracts oyster larvae. The larvae appears to be able to "ingest" (feed upon) these elongated cells ($\geq 5$ μm) of bacteria which are observed to occur during that stage of growth. Moreover, an oyster product appears to induce LST reproduction, similar to lectins produced by *Halachondrea panicea*, which stimulate the bacterium, *Pseudomonas insolita*. The association between the present bacteria and oyster larvae may, therefore, involve a hormone-like stimulatory effect on, or function involved in, larval development and metamorphosis.

The preferred growth medium for the bacteria of this invention is brain heart infusion with about 3% NaCl, although other conventional growth media which meet the nutritional requirements set forth above will suffice. (Alternative media are set forth in the Examples under Organism and Culture Conditions.) It is also preferable that the oyster larvae be fed *Isochrysis galbana* and *Monochrysis lutheri* at a rate of about $2 \times 10^5$ cells/ml of culture per day. The ideal surface upon which the bacteria can be grown is cultch, although glass is just as effective and more commercially expedient. Materials such as plastics or aluminum are also satisfactory.

Since the LST strain is mutagenically altered in accordance with this invention using ICR 191 to obtain the DIF and HYP variants, each variant has its own unique characteristics. Specifically, the DIF bacterium, ATCC number 33887, produces a low molecular weight pigment ($\leq 30,000$ daltons) that readily diffuses into the water column, i.e., any body of water. It is preferable, therefore, that this bacterium is employed in a process to induce high proportions of oyster larvae to uniformly set on varying surfaces to promote enhanced, but undirected, set. Moreover, the DIF strain specifically produces increased amounts of pheomelanin. On the other hand, the HYP bacterium, ATCC number, 33888, produces amplified amounts of melanin and melanin precursors of high molecular weight ($\geq 100,000$ daltons) that do not readily diffuse into the water column. It is preferable that the HYP variant is employed in a method to induce setting on specific surfaces for high level production of oyster development, and for the recovery of higher amounts of the melanin and melanin precursor metabolic products such as, for example, melanin, DOPA, tyrosine, tyrosinase and related enzymes.

Notably, each of the bacterial strains produce high amounts of the exopolymer, an acid polysaccharide, which can be employed, for example, as a marine cement, a water-proofing substance and/or as an emulsifying agent.

In another embodiment of the present invention, a method has been provided for the recovery and purification of the pigments metabolically produced by the present bacteria. The pigment is a melanin macromolecule, a heteropolymer of a number of monmeric precursors, which results from a biosynthetic pathway in which the monooxygenase catalyzed product of tyrosine, DOPA, is polymerized to form the melanin pigment. To obtain pigment and the related metabolic products for purification in accordance with this method, particularly, melanin, pheomelanin, the precursor DOPA, tyrosine, tyrosinase and other related enzymes, bacterial cells are grown to the late logarithmic phase in a growth medium after which the supernatant containing pigment is collected and filtered. The resulting free filtrates are concentrated, for example, by evaporation and dialysis. Alternatively, pigments can be precipitated with about 1% potassium persulfate and about one volume of methanol and recovered, for example, by centrifugation. The collected samples are subsequently deproteinized, for example, by extraction with 0.4M perchloric followed by centrifugation. Further purification can be facilitated by conventional means such as, for example, column chromatography or ion-exchange chromatography to resolve fractions. The pigment fractions are subsequently identified, for example, by an Absorbance/Fluorescence monitor. Ultrapure tyrosinase products are obtained and characterized by high pressure liquid chromatography (HPLC). Alternatively, these shellfish inducers are ultrapurified for maximum activity by isoelectric focusing or electrophoresis.

In a further embodiment of this invention, an acid polysaccharide exopolymer which is metabolically produced by the present bacteria is isolated, for example, by solubilizing the polysaccharide in an acetone-alcohol solution. The exopolymer can be precipitated at water-solvent interface.

For a better understanding of the present invention with other and further objects, reference is made to the following experimental descriptions and examples.

EXAMPLES

MATERIALS AND METHODS

Organism and Culture Conditions

LST was isolated on Marine Agar (Difco 2216) slants. Cultures were grown in a gyratory water bath (New Brunswick Scientific Model G76), at a setting yielding 8.5 ppm dissolved oxygen, at 25° C. The media employed were Marine Broth (Difco 2216), AGMS Synthetic Medium and AG Synthetic Medium, formulated similarly to the AGMS but lacking methionine and serine. The exact composition of AGMS and AG broths is set forth below. Solid synthetic media were prepared by adding 1.5% Agar (Difco). LST did not grow on TCBS.

COMPOSITION OF THE AGMS AND AG SYNTHETIC MEDIA

The AGMS Synthetic Medium consists of two stock solutions:

| Stock #1: | |
|---|---|
| NaCl | 19.45 g/L |
| $Mg.Cl_2.6H_2O$ | 8.80 g/L |
| $Na_2SO_4$ | 3.14 g/L |
| $CaCl_2$ (anhydrous) | 1.80 g/L |
| KCl | 0.55 g/L |
| $NaHCO_3$ | 0.16 g/L |
| KBr | 0.08 g/L |
| $H_3BO_3$ | 0.022 g/L |
| $SrCl_2$ | 0.034 g/L |
| $NaSiO_3$ | 0.004 g/L |
| $NH_4NO_3$ | 0.0016 g/L |
| $Na_2HPO_4$ | 0.008 g/L |
| Ferric Ammonium Citrate | 0.10 g/L |

The salts solution is autoclaved at 121° C. for 15 min at 15 lbs pressure. Sterile solution was stirred to evenly distribute the precipitate formed.

| Stock #2: | |
|---|---|
| Aspartic Acid | 26.27 g/L |
| Glutamic Acid | 23.77 g/L |
| Methionine | 0.39 g/L |
| Serine | 17.16 g/L |

The pH of the Stock #2 solution was adjusted to 7.2–7.4 using 6N NaOH. Sterilization by autoclaving as above followed pH adjustment.

AGMS Medium consists of a mixture of 30 ml Stock #1 with 70 ml Stock #2.

AG Medium uses the amino acid pool given below:

| Stock #3: | |
|---|---|
| Aspartic Acid | 26.27 g/L |
| Glutamic Acid | 23.77 g/L |

Stock #1 and Stock #3 were mixed in the same proportions as for AGMS Medium (30-70) after adjusting the pH of the solution to 7.6 with 6N NaOH and sterilizing the solution.

| Stock #4: Phosphate Solution | |
|---|---|
| $K_2HPO_4$ | 13.6 g/L |
| $K_2HPO_4$ | 21.3 g/L |

Autoclave separately, add 0.46 ml/100 ml GAMS.

Synthetic Medium Development and Growth Curves

The AGMS Synthetic Broth sustained the growth of LST when supplemented with 2% NaCl (NaCl final concentration 3%). Using a drop-out series experiment, the contribution of each amino acid supplied in AGMS (aspartic acid, glutamic acid, methionine and serine) to the growth of LST was evaluated by direct microscopic counts (phase contrast 0.19 $\mu$m resolution) and by viable counts.

To approximate the growth rate of LST, turbidimetric measurements of cultures grown in Marine and AG broths were made over a period of 470 hrs using a Klett-Summerson Photoelectric Colorimeter with a green filter.

Morphology

Cell morphology during the growth cycle of LST was monitored under phase contrast microscopy (Series 10 AO Microscope 0.19 $\mu$m resolution). Scanning electron microscopy was used for a more detailed view of the structure of normal and aberrant LST cells. Bacterial cells were fixed according to a procedure described by Belas and Colwell (1982). To minimize the amount of inorganic precipitate, LST cells were grown for 48–96 hrs in AG Broth. The cultures were then centrifuged (Model PR-G IEC Refrigerated Centrifuge) at 2500×g for 10 min decanted, resuspended in 10 ml PBS and washed twice. After the final centrifugation, the pellets were resuspended in 10 ml PBS and 1 ml of 25% glutaraldehyde (Polysciences) was added. The mixtures were allowed to fix for 1 hr either at room temperature or overnight at 4° C. Following fixation, the bacterial suspension was passed through a 13 mm Swinex holder with a 0.2 $\mu$m Nucleopore filter, using a syringe attached to the Swinex. The volume that passed through each filter varied between 1 and 5 ml of culture suspension; care was taken to avoid damaging both fragile cell appendages and the filter. The syringe was then refilled with 5 ml of 0.2M cacodylate buffer with 2.5% glutaraldehyde; half the mixture was pushed through the filter, and the Swinex holder was sealed and stored overnight at 4° C. After fixation, dehydration was accomplished in seven steps, in which 5 ml EtOH (sequential concentrations of 30, 50, 70, 90 and 3×100%) were slowly passed through the filter over a period of 30–60 minutes.

Specimens were further prepared for microscopy as follows: The filters were critical point dried and placed cell side up on SEM stubs using double stick adhesives. To reduce charging of the specimen, small drops of silver paint were placed on four corners of the stub connecting the filter surface to the stub metal. The stubs were coated with Ag/Pd metal alloy in a sputter coater, and then stored for scanning electron microscopy in a dessicated environment.

To determine the presence and location of flagella on LST, the procedure of Mayfield and Innis (1977), a modification of Gray's stain, was used on wet mounts of motile bacteria. Stained cells were examined with phase contrast microscopy.

Figure 1:
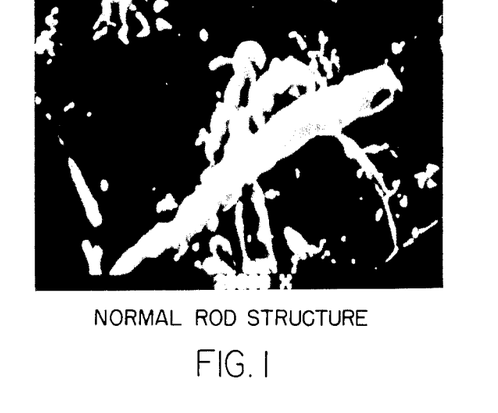
FIG. 1 is a scanning electron micrograph (10,000x) of a normal rod structure.
Figure 2:
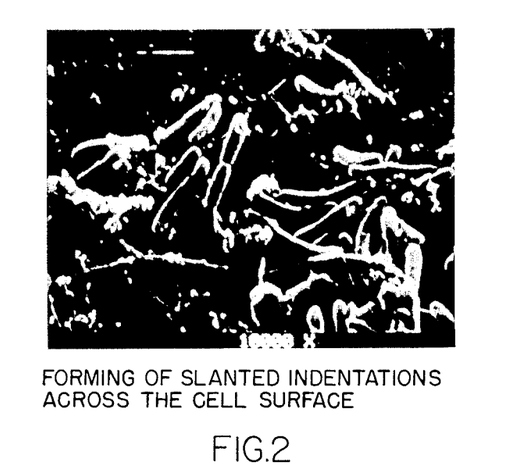
FIG. 2 is a scanning electron micrograph (20,000x) illustrating the formation of slanted indentations across the cell surface of the LST bacterium.

As anticipated, LST incurred a lengthy lag period (27 hrs) when transferred from Marine to AG medium. This lag period was not observed when cultures were transferred from AG to AG medium (FIG. 2). The generation time of LST at 25° C. was 4 hrs in marine broth and 7 hrs in AG Medium. The slower growth rate in the Synthetic Medium is presumably correlated to the availability of nutrients in the two media. All growth factors must have been synthesized de novo from glutamic and aspartic acids in AG, whereas Marine Broth was replete with numerous vitamins from Yeast extract and a wide variety of nutrients in peptone.

Mutagenesis

Ethyl Methane Sulfonate

To test the hypothesis that LST pigment attracts spat, pigment-less variants were desirable controls Consequently, LST was mutagenized with ethane methane sulfonate (EMS; Sigma) according to a modification of the procedure used by McCardell (1979). Logarithmically growing cultures of LST were suspended in 0.066M PBS to an approximate concentration of $2 \times 10^9$ cells/ml. EMS was added to 1 ml aliquots of culture to yield final concentrations ranging between 10–30 μl/ml (5 μl intervals). The resulting suspensions were incubated for 1 and 1.5 hrs in a G76 Water Bath Shaker (New Brunswick Scientific) at setting 5. The suspensions were diluted 1:10 in PBS, centrifuged, washed with 5 ml PBS and resuspended in 3 ml PBS. Two ml of the final suspension were inoculated in AG Broth and incubated 2–5 days. After this adaptation period, the mutagenized and recovered culture was then spread on Marine Agar. The remaining 1 ml of treated suspension was used to "spread plate" directly on AG and Marine agars. Screening of mutants was assessed visually, since pigment production was easily scored on agar plates.

Mutagenesis with EMS for 1 hr reduced the viability of LST 2–3 logs as determined by spread plate counts on Marine Agar (Table 6). No colonies formed on AG Agar when LST was "plated" directly after mutagenesis. This result was not unexpected: Since the minimal medium lacks so many growth factors, auxotrophic mutations would be conditionally lethal. Mutagenzied suspensions, after 2–5 days "holding" periods in AG Broth, were streaked on Marine and AG agars. Spread plate counts on Marine Agar ranged from $1.3-6.6 \times 10^9$, while they were approximately two logs lower on AG Agar: $1.4-6.5 \times 10^7$ (Table 6). The colonies on AG Agar were probably in part progeny of cells that remained in stasis in the AG Medium, repairing damage to the chromosome and possibly even back mutating.

Suspensions treated with EMS (all concentrations) for 1.5 hrs did not yield any colonies either after direct plating (Marine or AG agars), or after the holding period in AG Broth.

No pigment-less mutants were detected among the approximately 5000 colonies screened, on either undefined or minimal media. A number of factors may have led to this failure. Two of the possibilities, not mutually exclusive, are that pigment production is part of an obligate cell survival pathway, a serious consideration since melanin is part of the tyrosinase metabolism. In this case, obtaining pigment-less variants may prove an unrealistic goal. A second possibility is based on reports that pigment synthesis is essentially dependent upon a single enzyme, tyrosinase or a tyrosinase-like derivative. In this instance, mutations involving the mel gene would appear with very low frequencies. Furthermore, the likelihood of another mutational aberration that would be lethal to cells containing a lesion in a mel gene would be high. In any case, we had only screened about 5000 colonies by this procedure, and a mutation rate of less than 0.02% is not uncommon. Mutagenesis experiments using ICR 191 were designed with a holding period in Marine Broth rather than AG Broth to minimize auxotrophic lethality.

ICR 191

The procedures were modified slightly from those described above. The reaction mixture consisted of AG minimal medium containing 10% Marine Broth, $3-6 \times 10^8$ LST/ml and 10 μg ICR 191/ml. Cells were incubated at 30° C. in the reaction mixture for 12 hrs and then diluted 1:100 into fresh Marine Broth to provide an adaption period of between 12–72 hrs. Mutants were screened on Marine, AG and AGT agars.

A total of 24,803 colonies were screened. Thirty-nine colonies varied in pigmentation, seven had no pigment (hypo), two were darker (hyper), including the HYP variant, two were light tan, 27 were various shades of red from which the DIF variant was isolated and one was yellow. The paucity of pigment mutations suggested that either only a single enzyme was necessary for pigmentation (or any one of two or more enzymes) or that somehow pigmentation was somehow linked to viability. The first of these two hypotheses is consistent with the pigment being a melanin. These results also suggest that LST may produce more than one pigment, the lighter ones being masked by the brown ones. Also interesting, the seven mel- or hypo "mutations" have not been stable, reverting on average about one in 3–10 generations.

About 83% of the colonies that grew in Marine Agar, grew on AG Agar revealing that a considerable fraction of auxotrophic mutations were produced. Inexplicably, only 66% of the colonies that grew on Marine Agar, grew on AGT Agar.

Pigment Isolation and Characterization

Crude pigment was obtained from broth cultures that had been grown for at least 48–72 hrs (to stationary phase) in either Marine or AG broths. Spent medium was centrifuged at $2500 \times g$ for 15 min to remove the cells. The supernatants were dialyzed against distilled water for 24 hrs and pigment was purified by gel filtration.

Sephadex G-50, G-75 and G-150 columns (Pharmacia Chemicals), in which the dextran beads were swollen in distilled water in 0.02% sodium azide to prevent microbial growth, were calibrated with lysozyme, tripsinogen, egg albumin, bovine albumin and yeast alcohol dehydrogenase standards obtained from Pharmacia. Running buffer consisted of distilled water with 0.02% sodium azide, adjusted to pH 8.5. Void volume was determined using blue dextran 2000. The fractions were monitored at 280 nm.

The pigment fractionation was carried out on an Isco Model 328 Fraction Collector, using an ISCO Type 6 Optical Unit and an ISCO Model UA-5 Absorbance/Fluorescence Monitor to identify the pigment fractions.

The optical densities of the Sephadex fractions were analyzed using a Model 25 Beckman Spectrophotometer in the scan mode (200 through 750 nm). In general, melanin had a much lower extinction coeffecient in the visible range than in the ultraviolet, making dilutions of the samples necessary for analysis in the range of 200–350 nm. The absorption spectra of glutaraldehyde-treated cultures were also determined. Using a second basic method of extraction, crystallized pigment was obtained by a procedure in which the liquid phase of a culture supernatant was boiled off and the "residue" was dried at 90° C.

Another experiment was designed to determine whether a significant amount of pigment was cell-associated, or whether most of the pigment was excreted. Cell pellets (2500×g, 15 min) were resuspended in phosphate buffered saline (PBS), sonicated at low speed (setting 30) for 30 seconds (Bronwill Biosonk IV Sonicator) and recentrifuged. This pigment preparation was compared spectrophotometrically to a culture, containing both cells and soluble pigment, treated in the same way with sonication. Standard solutions of melanin (Sigma) at a concentration of 0.25 mg/ml distilled $H_2O$ and L-DOPA (Sigma) at a concentration 1.0 mg/ml were compared with the absorbance spectra of LST culture pigments.

Pigment solubilities were preliminarily tested, using 0.5 ml culture supernatant to 2.5 ml solvents. The solutions were agitated and maintained for at least 30 min after which they were centrifuged to separate potential precipitates. The criteria of Zussman, et al. (1960) were adopted to describe the solubility of pigment in the solvents. Pigments were designated "soluble" if they dissolved in the solvent, "slightly soluble" if the solvent became colored but the pigment did not dissolve, and "insoluble" if no color was imparted to the solvent. Solvent-pigment combinations were also examined by spectrophotometer.

Infrared (IR) spectra were determined (Perkin Elmer 281 IR spectrophotometer). Experimental samples were column purified, dialyzed, freeze dried LST pigment from culture supernatant to which one drop of paraffin oil was added. Commercially obtained melanin (Sigma), synthesized via the photooxidation of L-DOPA, was used as a control.

After LST cultures reached stationary phase, a soluble pigment, ranging in color from reddish-brown to dark brown, became evident. It was retained in dialysis and was precipitated by acidified water, ethanol and methanol (Table 4). The pigment was relatively soluble in water, only slightly soluble in ethanol and methanol and insoluble in acetone, chloroform, cyclohexane and ethylene dichloride.

Figure 3:
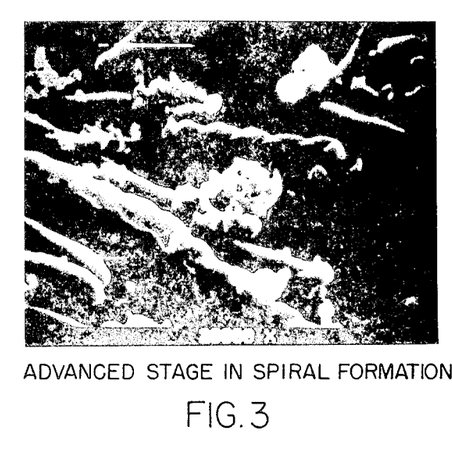
FIG. 3 is a scanning electron micrograph (20,000x) illustrating the advanced stage of spiral formation of the LST bacterium.

The crude pigment exhibited three maximum absorbance intervals at 260, 407 and the largest at 220 nm (Table 5, FIG. 3). Glutaraldehyde partially oxidized the pigment, shifting the absorbance peaks to 233, 273 and 435 nm. When the pigment was totally oxidized, it appeared darkest and an absorbance peak was shifted still further from 273 to 293 nm. Additionally, there was generalized absorption in the visible region.

Figure 4:
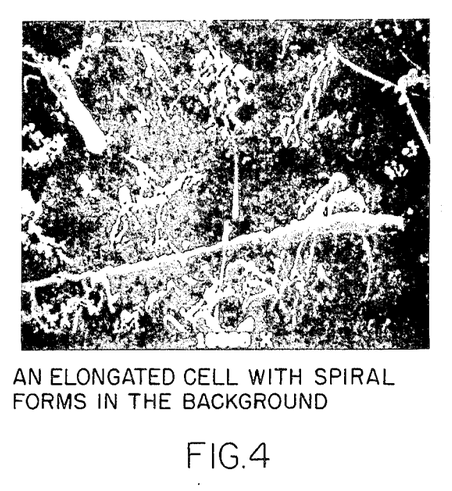
FIG. 4 is a scanning electron micrograph (10,000x) illustrating an elongated cell of the LST bacterium with spiral forms shown in the background.
Figure 5:
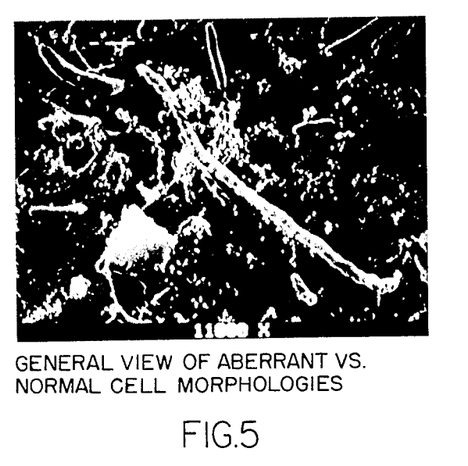
FIG. 5 is a scanning electron micrograph (11,000x) illustrating a general view of aberrant and normal cell morphologies of the LST bacterium.
Figure 6:
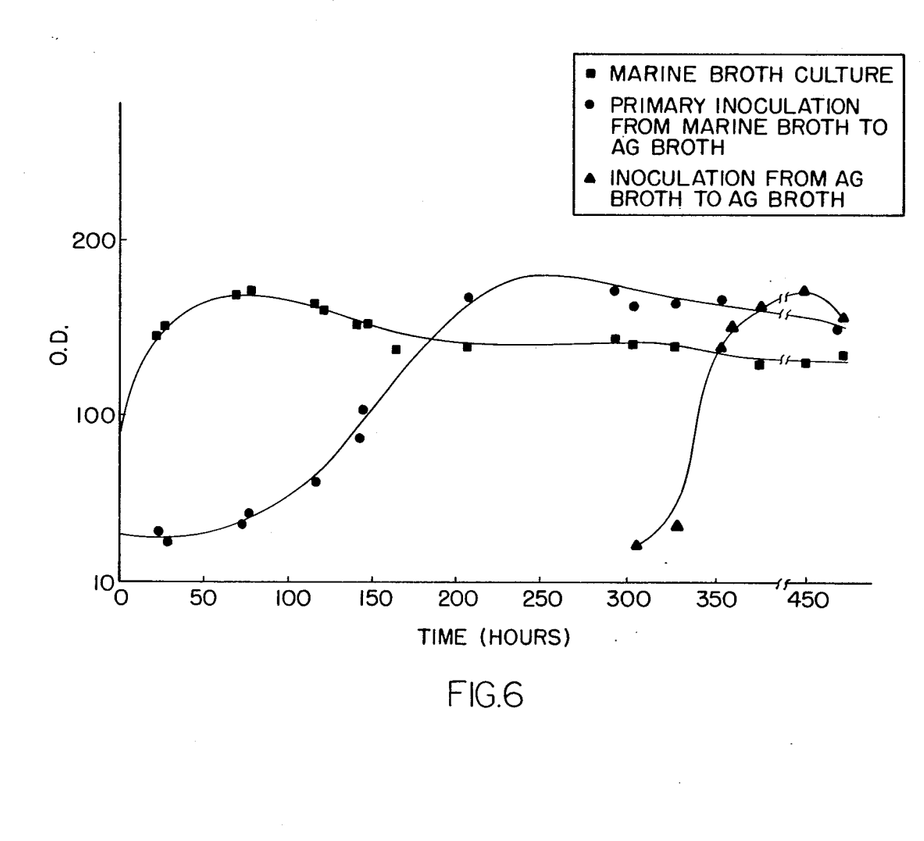
FIG. 6 is a graphic illustration depicting growth curves of LST cultures grown in Marine and AG synthetic broths.
Figure 7:
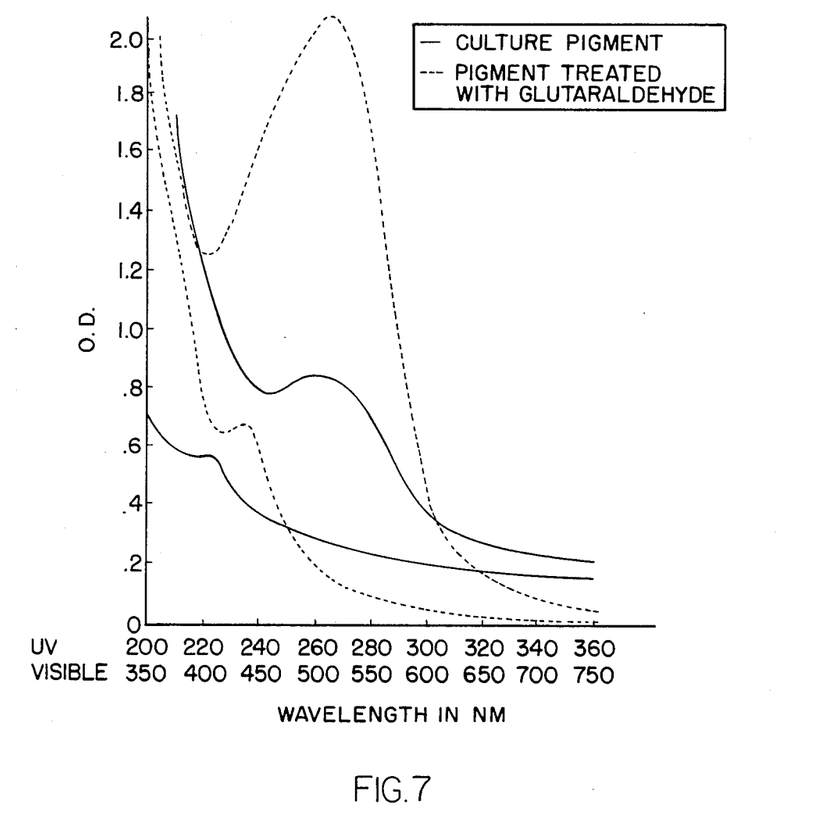
FIG. 7 is a graphic illustration depicting the absorbance spectra of culture pigment and a glutaraldehyde-treated pigment.
Figure 8:
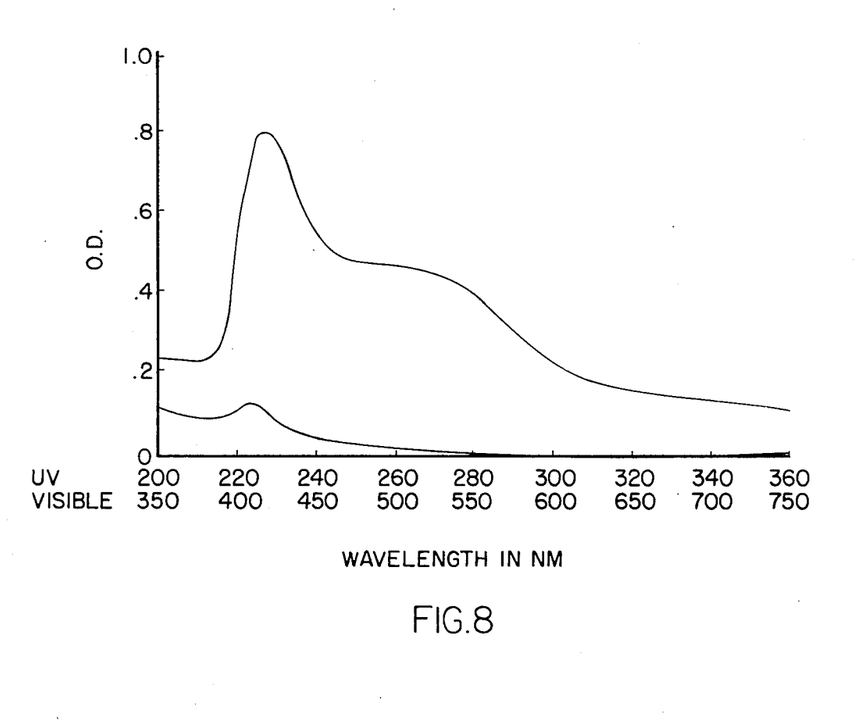
FIG. 8 is a graphic illustration depicting the absorbance spectrum of a pigment fraction purified on a Sephadex G-75 column.
Figure 9:
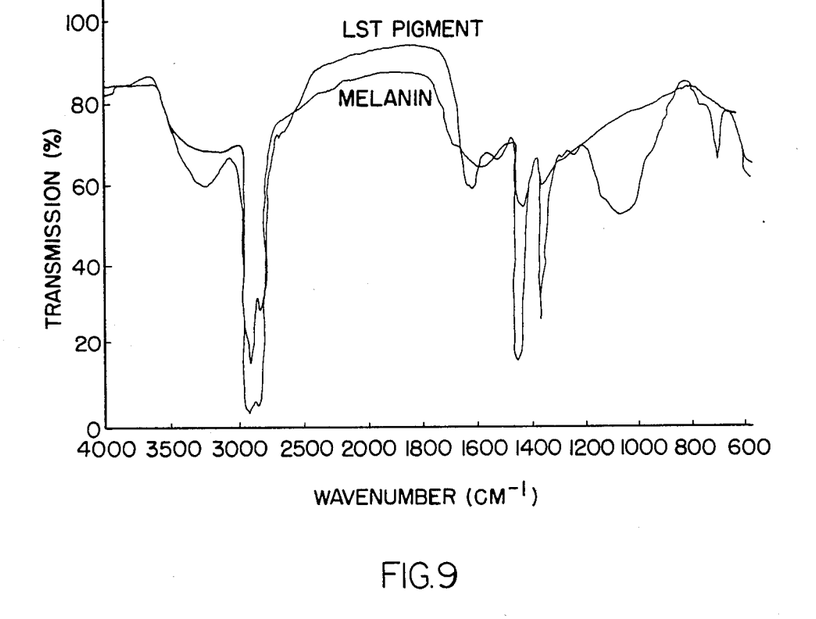
FIG. 9 is an IR spectrum pattern of melanin and LST pigment.

The absorption spectra of the experimental LST pigment was compared with spectra of commercial melanin, which had peaks at 225 and 273 nm, and with L-DOPA, which had peaks at 233, 282 and 512 nm. The LST product absorbance maxima were deemed to sufficiently match those of the commercial preparation to conclude that LST did indeed produce a melanin. Further purified LST pigments tended to support that hypothesis. Pigment fractions obtained from Sephadex G-75 and G-150 columns yielded absorbance maxima at 226, 263 and 407 nm (FIG. 4). A peak in the visible region was not detected in the commercial pigment preparation, possibly due to the consequence of the low solubility of melanin (viz., a particle-free suspension was not sufficiently concentrated).

Shellfish Attachment

Three spat setting tanks were filled with seawater (25° C.) and presetting (eyed) oyster larvae. Acid cleaned (1N HCl, 24 hrs) and sterilized glass slides were immersed in Set Tank 1. Glass slides, categorized and treated as follows, were placed in Set Tank 2:

1. Pigmented LST: Slides were immersed for 24 hrs in a stationary phase culture of LST, grown in Marine Broth at 25° C.
2. UV irradiated LST: Slides were immersed for 24 hrs in a late stationary phase culture of LST, grown in Marine Broth at 25° C. The slides were then exposed to lethal doses of UV radiation.
3. Marine Broth control: Slides were immersed in uninoculated media for 24 hrs.

In Set Tank 3, plates and glass slides were treated in the following manner:

1. 10 mg DOPA per 10 ml 2% noble agar.
2. 50 mg DOPA per 10 ml 2% noble agar.
3. 100 mg DOPA per 10 ml 2% noble agar.
4. 10 mg commercial melanin per 10 ml 2% noble agar.
5. 20 mg commercial melanin per 10 ml 2% noble agar.
6. 10 ml noble agar (control).
7. Culture pigment: An LST culture in the late stationary phase of growth (Marine Broth at 25° C.) was centrifuged (2500×g, 10 min) and the supernatant filtered through 1.2 μml Millipore filters to further remove cells. Slides were immersed in the cell-free filtrate for 24 hrs.

After 24 hrs in the setting tanks, all slides and plates were removed and the attached spat were counted using a stereoscope (10X; Baush and Lomb).

One caveat must be noted. The pigment coated slides and all of the Agar plates were placed in one tank. The DOPA dissolved in the water (high solubility, large water volume), autooxidized, and a thin deposit coated all the plates, slides and tank surfaces. Thus, the attached spat population may have been enhanced.

Data such as those reported in Tables 7 and 8, together with other evidence, supports the notion that LST pigment promotes shellfish attachment. Slides coated with pigmented LST attracted more than 5 times the oyster spat than the clean and control slides (Tables 7 and 8). Interestingly, slides coated with UV-irradiated LST attracted slightly less spat than the controls, possibly because the melanin was photooxidatively degraded.

The data involving Agar plate imbedded with the test substance and glass slides coated with culture pigment are to be interpreted much more cautiously, since the DOPA diffused out of the Agar, autooxidized, infiltrated the tank and interfered with experimental gradients. Nevertheless, melanin Agar plates also attracted more spat than the control plates, while DOPA Agar plates attracted 2-5 times less spat than the controls. The number of spat (attached oysters) was inversely proportional to the concentration of DOPA in the Agar, suggesting that at high concentrations, DOPA may have a repelling effect on the shellfish. The pigment coated slides, placed in the same tank with the Agar plates, attracted almost 10 times the number of spat attached to the control slides.

Isolation and Purification of Acid Polysaccharide Exopolymer

LST, DIF and HYP in 3% brain heart infusion agar (3 BHI) secretes an acid polysaccharide exopolymer amounting to approximately 500% of the weight of the bacterium in 48 hrs at 25° C. This exopolymer is isolated as follows:

1. 3 BHI in large petri plates is inoculated with 1 ml of $10^8$ LST, DIF or HYP grown as described above.

2. The cultrue is incubated for 2 days.

3. The acid polysaccharide exopolymer is solubilized in an acetone-alcohol solution.

4. The exopolymer is precipitated at the water-solvent interface.

Larval Induction

LST, DIF and HYP are grown in a conventional growth vessel fermentator (NBC CMF 128S) filled to 15 liters. A series of these vessels accomodates coated cultch or slides to induce the metamorphosis of 10,000 spat.

The bacterial cells are grown as indicated above and slides are immersed in the growth vessel. The bacteria affix to the slides via the adhesive exopolymer they produce.

The bacteria-coated surfaces are removed from the fermentor and placed at the bottom of a larval set tank. Larvae are exposed to the bacteria in filtered, slow moving water. The steady state setup can remain active for months. The activated cultch or slides are restored each new setting season Salinities range from 1.8 to 2.5%.

The oysters are fed *Isochrysis galbana* and *Monochrysis lutheri* at a rate of approximately $2 \times 10^5$ cells/ml of culture per day.

Thus, while the invention has been described with reference to certain preferred embodiments, those skilled in the art will realize that changes and modifications may be made thereto without departing from the full and intended scope of the appended claims.

TABLE 1

Some biochemical and physical characteristics of LST

| Test | Reaction |
|---|---|
| Gram stain | gram neg |
| Cell shape | rod |
| Spores | − |
| Motility | + |
| Catalase | + |
| Lysine decarboxylase | + |
| Ornithine decarboxylase | − |
| Sucrose fermentation | − |
| Mannose fermentation | − |
| Arabinose fermentation | − |
| Growth in 2.5% NaCl | + |
| Growth in 5.0% NaCl | + |
| Growth in 7.5% NaCl | + |

TABLE 2

Contributions of aspartic acid (asp), glutamic acid (Glu), methionine (Met) and serine (Ser) to the growth of LST[a]

| Amino Acids | Growth[b] |
|---|---|
| Asp Glu Met | +++ |
| Asp Met Ser | +++ |
| Glu Met Ser | +++ |
| Asp Ser | +++ |
| Ser Met | − |
| Asp Glu | +++ |
| Asp Met | + |
| Ser Glu | ++ |
| Glu Met | ++ |

[a]Inorganic salts solution (Appendix I) was supplemented with each of the amino acids listed in the concentrations used in the AGMS medium.
[b]+++, ~7 hr generation time; ++, ~10 hr generation time; +, ~13 hr generation time; −, no growth.

TABLE 3

Adenosyl nucleotide pool in a hypo-pigment producing varient of LST cultivated in batch culture[a]

| Growth Phase | Viable Count (cfu/ml) | Morphology | AEC[b] | pM ATP/Cell | μg/Cell[c] |
|---|---|---|---|---|---|
| Log | $4.5 \times 10^7$ | Short Rods | 0.86 | $1.19 \times 10^{-7}$ | $6.56 \times 10^{-11}$ |
| Stationary | $2.9 \times 10^9$ | Rods | 0.80 | $1.73 \times 10^{-9}$ | $9.53 \times 10^{-13}$ |
| Stationary-Decline | $2.7 \times 10^7$ | Long Spirals | 0.72 | $1.61 \times 10^{-9}$ | $8.86 \times 10^{-13}$ |

[a]Cells were removed from a batch culture of LST during log phase, stationary phase and during the stationary-decline transition and were then frozen (−70° C.). Adenoxyl nucleotides were extracted in boiling tris. The samples were then assayed for ATP, ADP and AMP and adenylate energy charge (AEC) was calculated.
[b]Calculations were based on known internal standards that revealed recovery and counting efficiencies if 72.4% for ATP, 41.6% for ADP, 38.0% for AMP.
[c]μg ATP per cell was calculated by multiplying pM/cell by $10^{-6}$ and by ATP mol. wt.

TABLE 4

Solubility of LST excreted pigment (in spent medium) in seven solvents

| Solvent | Solubility[a] | Precipitate[b] | Absorbance[c] Maxima |
|---|---|---|---|
| H$_2$O, pH 3 | S | +(24 h) | 264, 401 |
| H$_2$O, pH 9 | S | − | 264, 407 |
| Acetone | I | +(30 s) | none |
| Ethanol | SS | +(30 s) | 254, 375 |
| Methanol | SS | +(30 s) | 246, 264, 400 |
| Ethylene dichloride | I | − | 233, 264, 400 |
| Chloroform | I | − | 243, 276 |
| Cyclohexane | I | − | 203, 222 |

[a]S-relatively soluble; SS-slightly soluble; I-insoluble
[b]+ Precipitate formed (time at which formed) − No precipitate formed
[c]Absorbance maxima of pigment-solvent mixtures vs. solvent references

TABLE 5

Spectral absorbances of pigments extracted from LST

| Sample | Dilution | Absorbance Maxima[a] | Optical densities at Abs. Maxima |
|---|---|---|---|
| Marine Broth | 1:8 | 260 | 1.10 |
| Supernatant | 1:4 | 407 | 0.50 |
| LST-Associated | 1:16 | 264 | 0.36 |
| Pigment | 1:4 | 407 | 0.33 |
| LST-Associated and | 1:64 | 260 | 0.38 |
| Soluble Pigment | 1:4 | 407 | 0.25 |
| Red-Black Pigment | 1:64 | 237 | 1.08 |
| Treated w/Glut[b] | 1:1000 | 293 | 0.24 |
| Dark Orange Pigment | 1:64 | 234 | 1.34 |
| -Glut- | 1:64 | 272 | 0.58 |
|  | 1:4 | 436 | 0.60 |
| Yellow Pigment | 1:64 | 232 | 1.17 |
| -Glut- | 1:64 | 274 | 0.38 |
|  | 1:4 | 434 | 0.22 |
| Orange Pigment | 1:64 | 265 | 2.00 |
| -Glut- | 1:2 | 436 | 0.34 |
| Crude Pigment | 1:4 | 256 | 1.16 |
| Extract[c] | none | 405 | 0.11 |

TABLE 5-continued

Spectral absorbances of pigments extracted from LST

| Sample | Dilution | Absorbance Maxima[a] | Optical densities at Abs. Maxima |
|---|---|---|---|
| Commercial Melanin | 1:4 | 225 | 0.43 |
| 0.25 mg/ml | 1:4 | 273 | 0.31 |
| Commercial L-DOPA | 1:4 | 233 | 3.00 |
| 1.0 mg/ml | 1:4 | 282 | 2.90 |
| | none | 512 | 0.37 |

[a]There were 2-3 maxima for each sample. See text and FIG. 3 legend for further detail.
[b]Gluteraldehyde, an SEM fixative.
[c]Crude pigment extract was obtained by redissolving crude pigment crystals in distilled water to solubility limit (exact concentration unknown).

TABLE 6

Toxicity of Ethyl Methane Sulfonate (EMS) to LST[a]

| EMS Conc. ug/ml | Direct Growth[b] MA | Direct Growth[b] AG | Growth after Holding[c] MA | Growth after Holding[c] AG |
|---|---|---|---|---|
| 10 | $3.7 \times 10^6$ | No Data[d] | $1.4 \times 10^9$ | $1.5 \times 10^7$ |
| 15 | $1.3 \times 10^6$ | " | No Data | No Data |
| 20 | $7.0 \times 10^7$ | " | $6.6 \times 10^9$ | $6.5 \times 10^7$ |
| 25 | $6.9 \times 10^7$ | " | $3.2 \times 10^9$ | $2.1 \times 10^7$ |
| 30 | $7.1 \times 10^7$ | " | $1.3 \times 10^9$ | $1.4 \times 10^7$ |
| original culture | $6.7 \times 10^9$ | $3.8 \times 10^9$ | — | — |

[a]LST was exposed to EMS concentrations for 1 hr.
[b]Mutagenized suspensions were spread on plates immediately after exposure to EMS.
[c]Aliquots of mutagenized suspensions were "held" in AG Broth for 2-5 days, after which they were spread on Marine (MA) and AG agars.
[d]The dilutions plated did not yield any colonies.

TABLE 7

Density of Crassostrea virginica larvae attached to glass and agar surfaces

| Slide or Agar Plate Preparation[a] | Attached Spat Density[b] |
|---|---|
| Clean and Marine Broth Control Slides (I) | 0.11/in² (16) |
| Pigmented LST (II) | 0.58/in² (16) |
| UV Irradiated LST (II) | 0.07/in² (16) |
| Culture Pigment (III) | 1.00/in² (10) |
| 10 mg DOPA/10 ml agar (III) | 1.03/in² (2) |
| 50 mg DOPA/10 ml agar (III) | 0.42/in² (2) |
| 100 mg DOPA/10 ml agar (III) | 0.42/in² (2) |
| 10 mg melanin/10 ml agar (III) | 2.22/in² (2) |
| 20 mg melanin/10 ml agar (III) | 2.55/in² (2) |
| Agar Control/10 ml agar (III) | 2.12/in² (2) |

[a]Number in parentheses designates the spat tank used.
[b]Number in parentheses designates the number of samples taken.

TABLE 8

Attraction of Crassostrea virginica larvae by the bacteria LST, a melanin synthesizing species

| Sample Type[a] | Sample No.[b] | Mean No. Spat at 24 h[c] | 95% Confidence Interval[d] |
|---|---|---|---|
| Control[e] | 16 | 3.8 ± 1 | 1< >7 |
| Prefouled[f] | 27 | 24.8 ± 7 | 12< >38* |
| Hyphomonas neptunium[g] | 14 | 5.0 ± 2 | 2< >8 |
| LST[g] | 16 | 17.5 ± 3 | 12< >23* |
| Pigment from LST[g] | 10 | 30.0 ± 14 | 2< >58 |
| UV Killed LST[g] | 16 | 1.8 ± 1 | 0< >4 |
| Control[e] | 5 | 2.4 ± 1 | 2< >3 |
| LST[g] | 14 | 9.7 ± 1 | 7< >12* |
| LST Hypopigment producer[g] | 8 | 2.0 ± 1 | 1< >4 |

[a]First 6 samples were run on 1/81 and last 3 samples were run on 7/81 at the oyster mariculture unit in Lewes, Delaware.
[b]Chemically cleaned and sterilized 3 in × 1 microscope slides.
[c]Larval settlement and/or attachment per slide × 10. Standard error also shown.
[d]Asterisk denotes significant deviation from control samples.
[e]Placed in Marine medium for 24 hrs prior to immersion in oyster tank.
[f]Slides placed in mariculture holding tank (~$10^5$ viable bacteria/ml) prior to immersion in oyster tank.
[g]Slides were coated with sample type prior to immersion in oyster tank.

TABLE 9

LST properties of pigment compared with pigments identified as melanin of other microorganisms

| PROPERTIES | Aeromonas[a] liquefaciens | Vibrio[b] cholerae | Aspergillus[c] nidulans | LST[d] |
|---|---|---|---|---|
| Color | Brown-Black | Brown | Black | Brown |
| Solubility in H₂O at pH 7 | I | ND | ND | SS |
| Solubility in 0.1 N NaOH | S | S | S | S |
| Blackberg-Wanger Precipitation | PPT | PPT | ND | PPT |
| FeCl₃ Precipitation | PPT | PPT | PPT | PPT |
| Acid Precipitation | PPT | PPT | PPT | PPT |
| Reduction (Glutathione) | + | + | + | + |
| Reoxidation | + | ND | + | + |
| Absorption Peaks | Diffuse | 345,480 | 480,535 | 264,407 |
| H₂O Bleaching | ND | + | + | + |
| Molecular Weight | ND | ND | 2,000,000 | 120,000 |
| | | | 350,000 | 52,000 |
| | | | 29,000 | 12,000 |

I-insoluble; S-soluble; ND-no data; PPT-precipitated; +-positive
[a]Aurstad and Dahle 1972
[b]Ivins and Holmes 1980
[c]Bull 1970
[d]Present study

What is claimed is:

1. A biologically pure culture of bacteria, *alteromonas colwelii*, all having the identifying characteristics of ATCC number 33887 and mutants of said bacteria which induces the settlement and metamorphosis of *Crassostrea virginica* larvae.

2. A biologically pure culture of bacteria, *alteromonas colwellii* having all the identifying characteristics of ATCC number 33888 and mutants of said bacteria which induces the settlement and metamorphosis of *Crassostrea virginica* larvae.

* * * * *

UNITED STATES PATENT AND TRADEMARK OFFICE
CERTIFICATE OF CORRECTION

PATENT NO. : 4,740,466
DATED : April 26, 1988
INVENTOR(S) : Ronald M. Weiner, et al.

It is certified that error appears in the above-identified patent and that said Letters Patent is hereby corrected as shown below:

Column 9, line 13: "controls Consequently" should read as --controls. Consequently--

Column 12, line 25: "1.2 $\mu$ml" should read as --1.2 $\mu$m--

Column 14, Table 3, subject b: "counting efficiencies if 72.4%" should read as --counting efficiencies of 72.4%--

Column 16, line 60: "all having" should read as --having all--

Column 16, line 60, Claim 1: "colwelii" should read as --colwellii--

Column 16, line 65, Claim 2: "colwellii having" should read as --colwellii, having--

Signed and Sealed this

Thirtieth Day of May, 1989

*Attest:*

DONALD J. QUIGG

*Attesting Officer*     *Commissioner of Patents and Trademarks*